US012667671B2

(12) United States Patent
Ben-Ari

(10) Patent No.: US 12,667,671 B2
(45) Date of Patent: Jun. 30, 2026

(54) SYSTEM AND METHOD FOR INFORMATION MANAGEMENT IN COMPUTERIZED INJECTORS

(71) Applicant: PFIZER INC., New York, NY (US)

(72) Inventor: Ozi Ben-Ari, Kibbutz Ayelet Hashahar (IL)

(73) Assignee: PFIZER INC., New York, NY (US)

( * ) Notice: Subject to any disclaimer, the term of this patent is extended or adjusted under 35 U.S.C. 154(b) by 693 days.

(21) Appl. No.: 18/016,184

(22) PCT Filed: Jul. 12, 2021

(86) PCT No.: PCT/IB2021/056230
§ 371 (c)(1),
(2) Date: Jan. 13, 2023

(87) PCT Pub. No.: WO2022/013707
PCT Pub. Date: Jan. 20, 2022

(65) Prior Publication Data
US 2023/0263960 A1     Aug. 24, 2023

Related U.S. Application Data

(60) Provisional application No. 63/052,562, filed on Jul. 16, 2020.

(51) Int. Cl.
*A61M 5/315* (2006.01)
*A61B 90/98* (2016.01)

(52) U.S. Cl.
CPC ......... *A61M 5/31566* (2013.01); *A61B 90/98* (2016.02)

(58) Field of Classification Search
CPC ............... A61M 5/31566; A61M 5/20; A61M 2005/2407; A61M 2005/2492;
(Continued)

(56) References Cited

U.S. PATENT DOCUMENTS

2006/0120751 A1    6/2006  McVicker
2007/0191690 A1*   8/2007  Hasse .................. A61M 5/007
                                                            600/300
(Continued)

FOREIGN PATENT DOCUMENTS

WO      2006/108026      10/2006
WO      2014/143815       9/2014
(Continued)

OTHER PUBLICATIONS

International Search Report for International Application No. PCT/IB2021/056230, Mailed Oct. 6, 2021.
(Continued)

*Primary Examiner* — Lauren P Farrar

(74) *Attorney, Agent, or Firm* — DLA Piper LLP US

(57)                 ABSTRACT

The invention relates to a computer-controlled injector, comprising: a housing configured to receive a medicament cartridge; an injection drive mechanism comprising a computer-controlled motor for driving a piston within said medicament cartridge, for injecting the medicament; a data tag attachable to said medicament cartridge; and an electromagnetic detector disposed within said housing and being connectable to the data tag upon mounting of said medicament cartridge into said housing, said electromagnetic detector permitting data to be read from or written to said data tag. The electromagnetic detector is configured to read or write data irrespectively of a rotational orientation of said medicament cartridge within said computer-controlled injector.

17 Claims, 12 Drawing Sheets

(58) Field of Classification Search

CPC .......... A61M 2005/2496; A61M 2005/31588; A61M 2205/3317; A61M 2205/50; A61M 2205/6054; A61M 5/24; A61M 5/14566; A61M 5/31535; A61M 5/2422; A61M 5/31525; A61M 2205/52; A61B 90/98; G16H 20/17

See application file for complete search history.

(56) References Cited

U.S. PATENT DOCUMENTS

| | | | |
|---|---|---|---|
| 2007/0197974 | A1 | 8/2007 | Gibson |
| 2007/0198297 | A1 | 8/2007 | Perkins et al. |
| 2007/0208308 | A1 | 9/2007 | Gibson et al. |
| 2007/0208445 | A1 | 9/2007 | Gibson et al. |
| 2007/0225672 | A1 | 9/2007 | Wagner |
| 2007/0229266 | A1 | 10/2007 | Gibson |
| 2007/0235534 | A1 | 10/2007 | Fago et al. |
| 2007/0238989 | A1 | 10/2007 | Hasse et al. |
| 2007/0239112 | A1 | 10/2007 | Fago et al. |
| 2007/0241883 | A1 | 10/2007 | Fago et al. |
| 2007/0250414 | A1 | 10/2007 | Fago et al. |
| 2007/0257111 | A1 | 11/2007 | Ortenzi |
| 2007/0299421 | A1 | 12/2007 | Gibson |
| 2008/0147015 | A1 | 6/2008 | Ortenzi et al. |
| 2008/0208042 | A1 | 8/2008 | Ortenzi et al. |
| 2008/0211674 | A1 | 9/2008 | Gibson et al. |
| 2010/0256536 | A1* | 10/2010 | Novak .................. A61B 90/98 601/4 |
| 2015/0202367 | A1 | 7/2015 | Plaschkes et al. |
| 2018/0098914 | A1 | 4/2018 | Mounce et al. |
| 2018/0133106 | A1 | 5/2018 | Mounce et al. |
| 2018/0236181 | A1 | 8/2018 | Marlin et al. |
| 2020/0119769 | A1 | 4/2020 | Carlsson |

FOREIGN PATENT DOCUMENTS

| | | |
|---|---|---|
| WO | 2016/033507 | 3/2016 |
| WO | 2017/212473 | 12/2017 |

OTHER PUBLICATIONS

Written Opinion for International Application No. PCT/IB2021/056230, Mailed Oct. 6, 2021.

Third Party Observation for PCT/IB2021/056230 dated Oct. 31, 2022 (15 pages).

\* cited by examiner

FIG. 4B 130
220
470
520
530
480
480
140
482
150
432
120
RFID
100
102
430

SYSTEM AND METHOD FOR INFORMATION MANAGEMENT IN COMPUTERIZED INJECTORS

CROSS-REFERENCE TO RELATED APPLICATION

This application is the National Stage filing under 35 U.S.C. 371 of International Application No. PCT/IB2021/056230, filed Jul. 12, 2021, which claims priority to U.S. Provisional Application No. 63/052,562, filed Jul. 16, 2020, which are incorporated by reference in their entireties.

This application is related to U.S. patent application Ser. No. 14/423,834, filed Sep. 3, 2013, now U.S. Publication No. US20150202367, published Jul. 23, 2015, the disclosure of which is incorporated by reference in its entirety.

This application is also related to U.S. Provisional Patent Application No. 62/345,897, filed Jun. 6, 2016, the disclosure of which is incorporated by reference in its entirety.

This application is also related to PCT Patent Application No. PCT/IL2017/050607, filed Jun. 1, 2017, now PCT Publication No. WO2017212473, published Dec. 14, 2017, the disclosure of which is incorporated by reference in its entirety.

This application is also related to U.S. Provisional Patent Application No. 62/977,746, filed Feb. 18, 2020, the disclosure of which is incorporated by reference in its entirety.

FIELD OF THE INVENTION

The present invention generally relates to a computerized injector, and more specifically to a system and method for information management in computerized injectors, adapted for administration of medication to a patient.

BACKGROUND OF THE INVENTION

Many computerized injectors adapted for administration of medication to a patient are known. Various systems and methods for information management in multiple-use computerized injectors are also known.

Medicament cartridges containing a medicament to be ejected into a patient sometimes have a data tag attached thereto. It is advantageous to identify the medicament cartridge that is inserted into the multiple-use computerized injector.

SUMMARY OF THE INVENTION

The present invention seeks to provide an improved computerized injector.

There is thus provided in accordance with an embodiment of the present invention a computer-controlled injector, comprising: a housing arranged along a longitudinal axis and configured to receive a medicament cartridge; an injection drive mechanism including a computer-controlled motor for driving a piston, forming part of the medicament cartridge, for injecting a medicament; a data tag attachable to the medicament cartridge; and an electromagnetic detector disposed within the housing and being connectable to the data tag upon mounting of the medicament cartridge into the housing, the electromagnetic detector permitting data to be read from or written to the data tag; and wherein the electromagnetic detector configured to read or write data to the data tag irrespectively of a rotational orientation of the medicament cartridge within the computer-controlled injector.

Further, in accordance with an embodiment of the present invention, a medicament delivery system, comprising: a computer-controlled injector arranged along a longitudinal axis and having a housing and an electromagnetic detector contained therewithin; a medicament cartridge having a data tag formed thereon; the electromagnetic detector being operative to communicate with the data tag upon mounting of the medicament cartridge into the computer-controlled injector such that the data tag is disposed in proximity with the electromagnetic detector; and wherein the electromagnetic detector configured to read or write data to the data tag irrespectively of a rotational orientation of the medicament cartridge within the computer-controlled injector.

Even further, in accordance with an embodiment of the present invention, a computer-controlled injector for use with a medicament cartridge, which has a medicament contained therewithin and a data tag attached thereto, the computer-controlled injector comprising: an injection drive mechanism including a computer-controlled motor for driving a piston, forming part of the medicament cartridge, for injecting a medicament; a medicament cartridge mounting portion configured to support the electromagnetic detector; the electromagnetic detector configured to read or write data to the data tag when the medicament cartridge is mounted onto the medicament cartridge mounting portion; and wherein the electromagnetic detector configured to read or write data to the data tag irrespectively of a rotational orientation of the medicament cartridge within the computer-controlled injector.

Preferably, the electromagnetic detector comprises a single antenna. Further preferably, the electromagnetic detector comprises an annular antenna.

Preferably, the housing comprises an opening at a forward end thereof and the medicament cartridge is adapted for axial insertion into the housing through the opening. Alternatively, a pivoting openable and closeable mounting portion is provided to the housing and adapted to receive the medicament cartridge. Further alternatively, the housing comprises an opening at a forward end thereof and the medicament cartridge is adapted for rotatable insertion into the housing through the opening.

BRIEF DESCRIPTION OF THE DRAWINGS

The present invention will be understood and appreciated more fully from the following detailed description, taken in conjunction with the drawings in which:

FIGS. 4A-4B are simplified respective planar side view and a sectional view illustration showing the medicament cartridge prior to axial mounting into the MUCI, sectional view being taken along lines B-B in FIG. 4A;

Figure 1A:
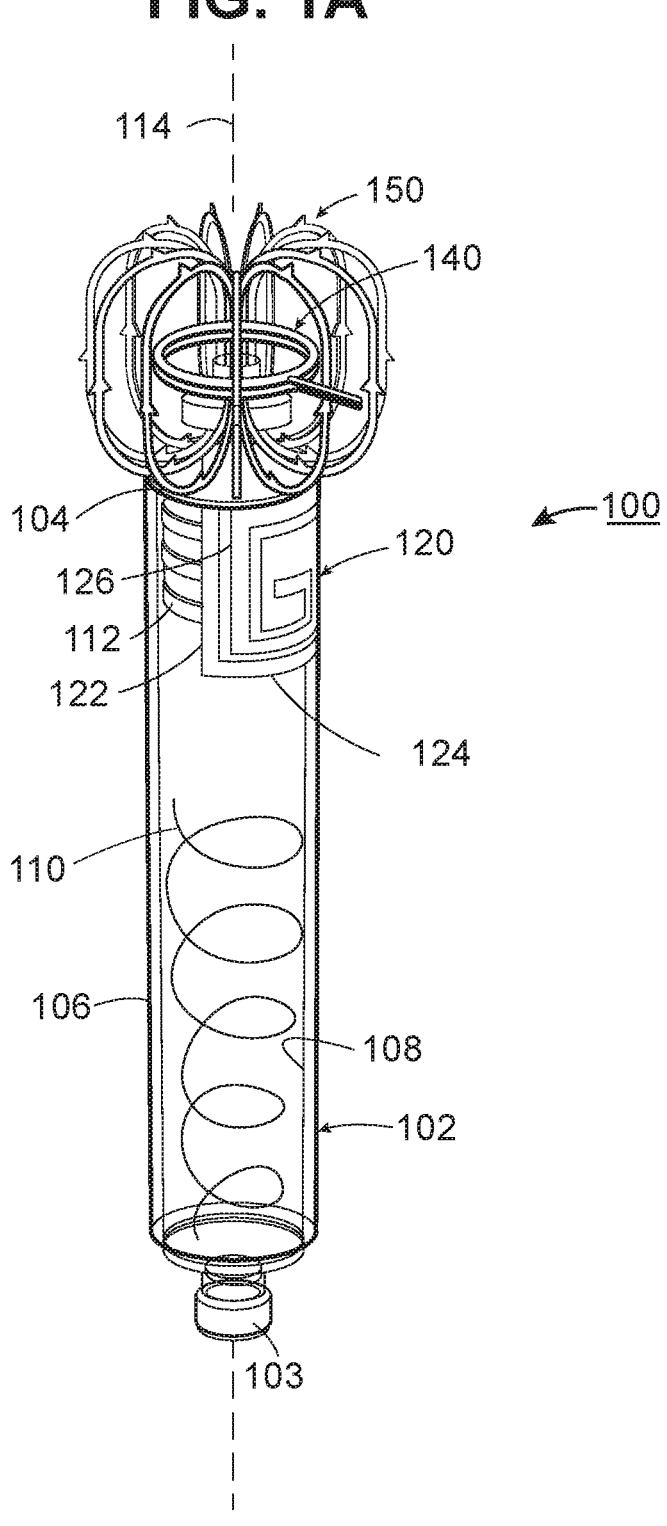
FIGS. 1A-1G are various simplified pictorial illustrations of a medicament cartridge to be used in conjunction with a multiple use computerized injector (MUCI) constructed and operative in accordance with an embodiment of the present invention.
Figures 1B, 1D, 1E:
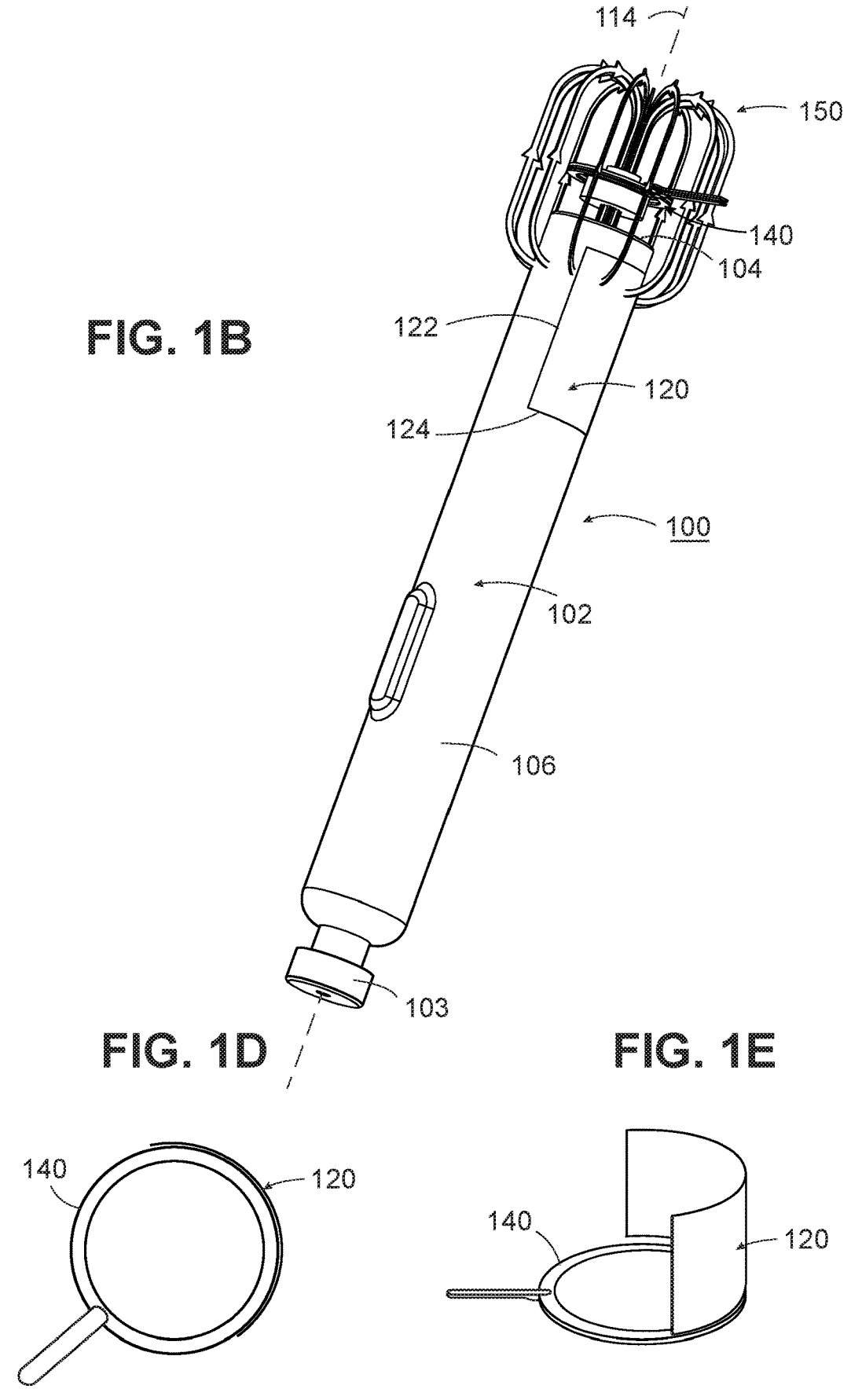
Figure 1C:
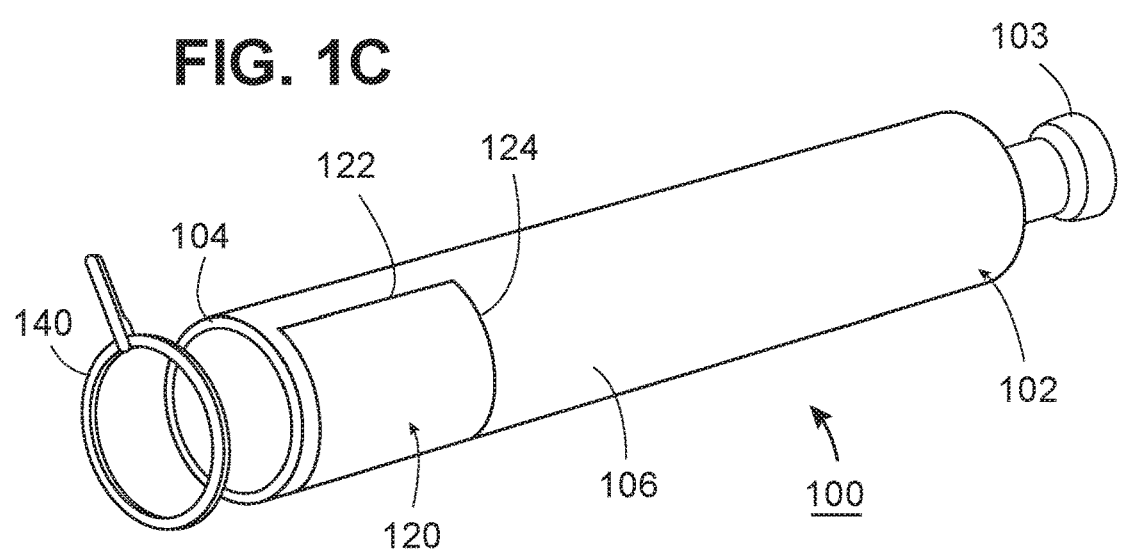
Figure 1F:
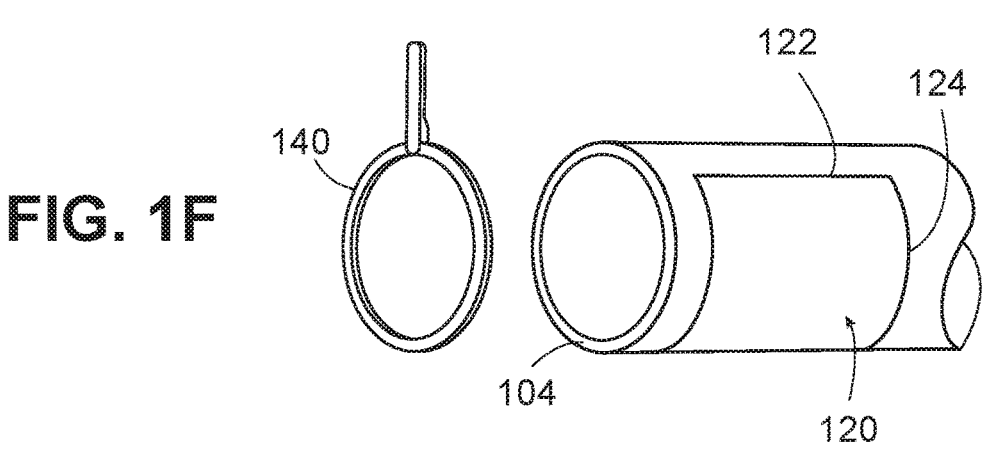
Figure 1G:
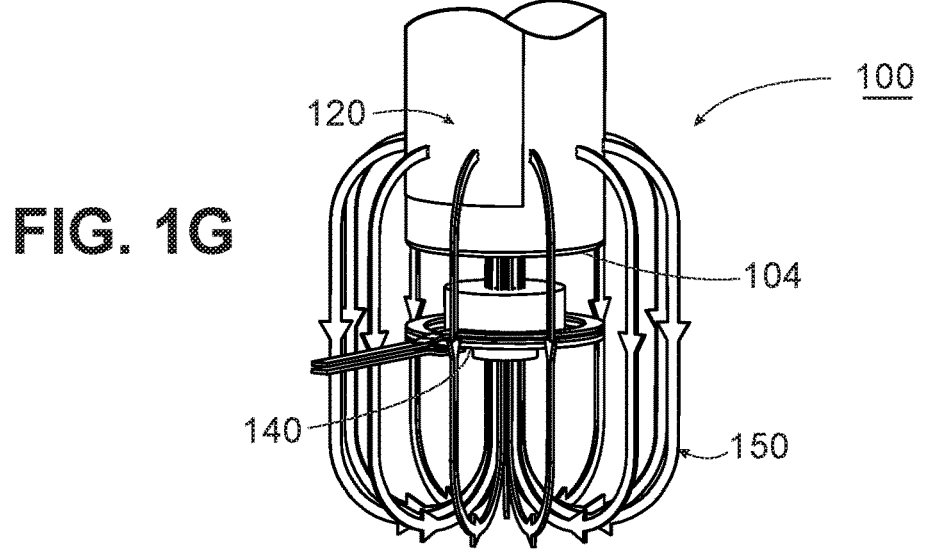

DETAILED DESCRIPTION OF EMBODIMENTS
OF THE INVENTION

A multiple use computerized injector (MUCI) comprises a housing arranged along a longitudinal axis and configured to receive a medicament cartridge; an injection drive mechanism including a computer-controlled motor for driving a piston, forming part of the medicament cartridge, for injecting a medicament; a data tag attachable to the medicament cartridge; and an electromagnetic detector disposed within the housing and being connectable to the data tag upon mounting of the medicament cartridge into the housing, the electromagnetic detector permitting data to be read from or written to the data tag.

Reference is now made to FIGS. 1A-1G, which are various simplified pictorial illustrations of a medicament cartridge to be used in conjunction with a multiple use computerized injector (MUCI) constructed and operative in accordance with an embodiment of the present invention.

A medicament cartridge 100 is shown is FIGS. 1A-1G. The medicament cartridge 100 has a generally cylindrical barrel 102 with a forward end including a resilient septum 103 and a generally circumferential rearward edge 104. The cylindrical barrel 102 defines an outer surface 106 and an inner surface 108. A medicament 110 is contained within the cylindrical barrel 102 and is sealed therewithin by a piston 112. The cylindrical barrel 102 is arranged along a longitudinal axis 114.

It is noted that any type of medicament container may be employed as part of an embodiment of the present invention, such as for example, pre-filled cartridges containing a liquid medication, dual-chamber cartridges containing a powder drug preparation and a solvent or any other suitable medicament cartridge 100.

A data tag 120 is attached to the outer surface 106 of the cylindrical barrel 102 and the medicament cartridge 100 is adapted to be mounted to a multiple use computerized injector (MUCI) 130. An example of such MUCI 130 is particularly shown and described with reference to FIGS. 2A-3D. The MUCI 130 is not shown in FIGS. 1A-1G for clarity purposes. The data tag 120 preferably includes a generally rectangular substrate having two long side walls 122 and two perpendicular short side walls 124 and an antenna 126 embedded thereon.

An electromagnetic detector 140 is configured to communicate with the antenna 126 of the data tag 120 formed on the medicament cartridge 100, as seen in FIGS. 1A-1G. It is noted that the electromagnetic detector 140 forms part of the MUCI 130. It is appreciated that the electromagnetic detector 140 communicates wirelessly with the antenna 126 of the data tag 120.

It is noted that the data tag 120 may contain various data fields, such as the name of the medicament, the ingredients, the viscosity and the expiry date. It is further noted that various data fields can be recorded to the data tag 120 during injection, such as the stroke of the piston within the barrel 102, rate of injection, remaining amount of medicament etc.

It is a particular feature of an embodiment of the present invention that the electromagnetic detector 140 is a single annular antenna. It is known that the electromagnetic field lines of an annular antenna have a doughnut-like shape, such as indicated by lines 150.

It is a further particular feature of an embodiment of the present invention that electric communication between the electromagnetic detector 140 in a form of an annular antenna and between the antenna 126 of the data tag 120 is enabled irrespectively of the rotational orientation of the medicament cartridge 100, due to the shape of the electromagnetic field lines formed by a substantially annular antenna 140.

Preferably, the medicament cartridge 100 is disposed within the MUCI 130 such that the rearward edge 104 of the medicament cartridge 100 is disposed in close proximity to the electromagnetic detector 140, thus enabling the maximal amount of electromagnetic flux from the electromagnetic detector 140 to reach the data tag 120.

The data tag 120 is preferably an RFID tag and is preferably attached to the outer surface 106 of the barrel 102. For optimal electrical communication between the antenna 126 of the data tag 120 and the electromagnetic detector 140, the data tag 120 is preferably placed adjacent the rearward edge 104. Alternatively, the data tag 120 may be attached at any other location on the outer surface 106 of the barrel 102.

It is seen in this embodiment of the present invention as seen in FIGS. 1A-1G that the electromagnetic detector 140 is slightly rearwardly spaced from rearward edge 104 of the medicament cartridge 100. In accordance with another embodiment of the present invention, the electromagnetic detector 140 may be arranged around the outer surface 106 of the medicament cartridge 100 and forwardly spaced therefrom and the data tag 120 is then attached to the outer surface 106 of the barrel 102 in such manner that it is either rearwardly or forwardly spaced from the electromagnetic detector 140, but does not overlap therewith to avoid interference between the electromagnetic field lines 150.

It is noted that the data tag may be passive, containing no power supply of its own or active, containing its own power supply.

The data tag 120 is a generally elongated element. In an example shown in FIGS. 1A and 1C-1G, the data tag 120 is attached to the barrel 102 and arranged in perpendicular to the longitudinal axis 114, such that long side walls 122 are disposed substantially in parallel to the rearward edge 104 of the medicament cartridge 100. In an example shown in FIG. 1B, the data tag 120 is attached to the barrel 102 and arranged along the longitudinal axis 114, such that long side walls 122 are disposed substantially in perpendicular to the rearward edge 104 of the medicament cartridge 100.

It is a particular feature of an embodiment of the present invention that the data tag 120 is preferably disposed such that the long side walls 122 are disposed substantially in parallel to the rearward edge 104 of the medicament cartridge 100, such as clearly shown in FIGS. 1C-1G. This orientation of the data tag 120 relative to the electromagnetic detector 140 provides for maximal surface of the antenna 126 to be disposed in parallel to rearward edge 104 of the medicament cartridge and thus the maximal surface of the antenna 126 is disposed in perpendicular to the electromagnetic field lines 150 of the electromagnetic detector 140. This fact enables maximization of the electromagnetic flux that reaches the antenna 126 of the data tag 120 by maximizing the surface area of the antenna 126 that is exposed to the electromagnetic flux.

It is a particular feature of an embodiment of the present invention that the data tag 120 is disposed on a plane, which is generally perpendicular to the plane of the electromagnetic detector 140, thus facilitating exposure of the data tag 120 to the electromagnetic field lines 150 of the electromagnetic detector 140 irrespectively of the rotational orientation of the medicament cartridge 100.

It is noted that the that the electromagnetic detector 140 is preferably annular. Alternatively, any circumferential or nearly circumferential shape of an antenna can be employed. Further alternatively, the electromagnetic detector 140 can be formed of a plurality of radially spaced segments forming an annular-like shaped antenna. Different shapes of electromagnetic detectors 140 may be associated with the MUCI 130, such as for example closed loop antenna or open loop antenna.

A single electromagnetic detector 140 in a form of an annular antenna is preferably employed in accordance with an embodiment of the present invention. Alternatively, any number of electromagnetic detectors 140 can be employed.

The diameter of the electromagnetic detector 140 is preferably equal or slightly larger than the diameter of the barrel 102. Alternatively, the diameter of the electromagnetic detector 140 may be slightly smaller than the diameter of the barrel 102.

It is appreciated that the size and shape of the electromagnetic detector 140 are chosen such that optimal electrical communication between the antenna 126 of the data tag 120 and the electromagnetic detector 140 is enabled.

Figures 2A, 2B:
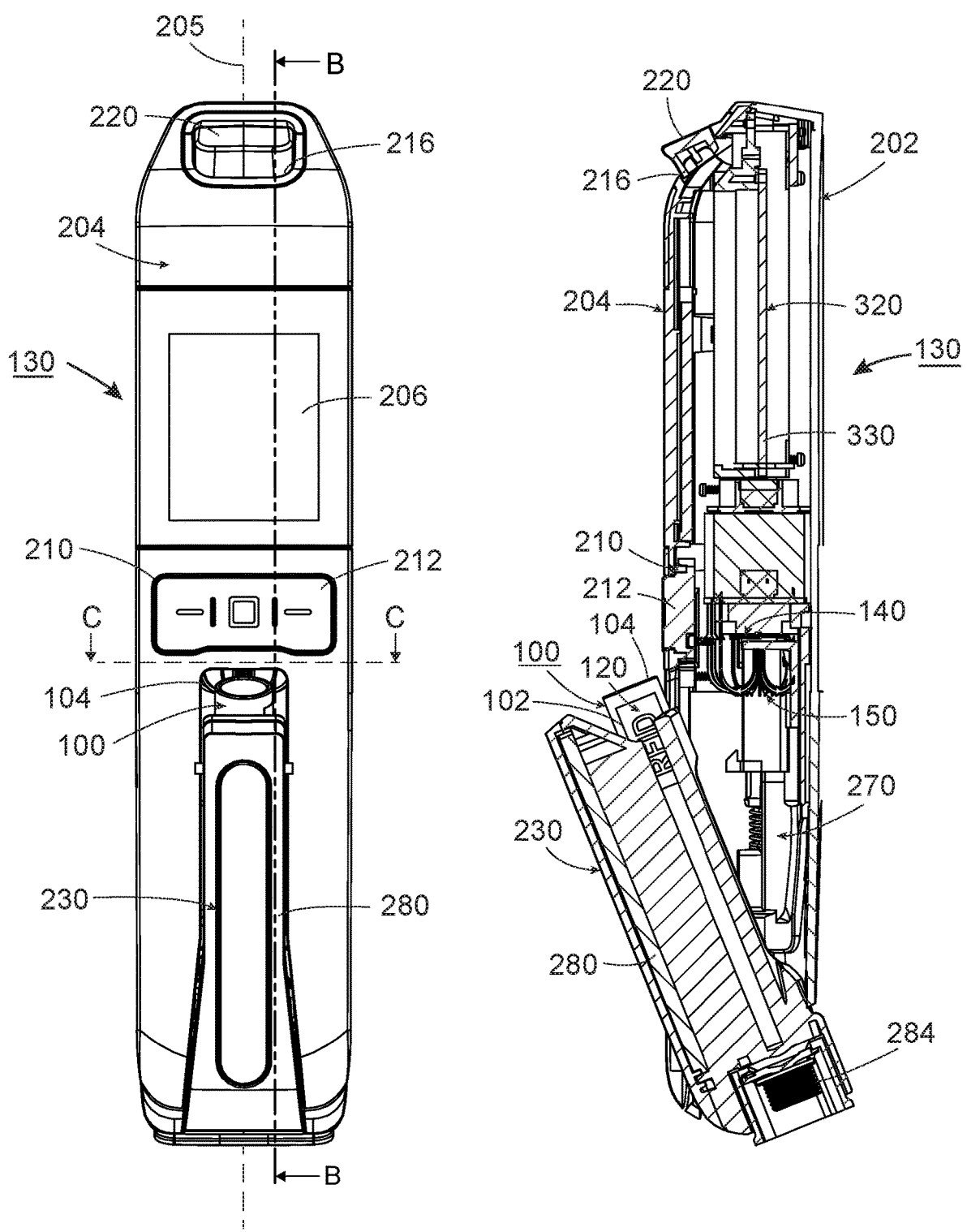
FIGS. 2A-2D are simplified respective planar front view, two different sectional views and a pictorial cut-out view illustrations showing the medicament cartridge prior to pivotable mounting into the MUCI, sectional views being taken along orthogonal lines C-C and D-D in FIG. 2A.
Figure 2C:
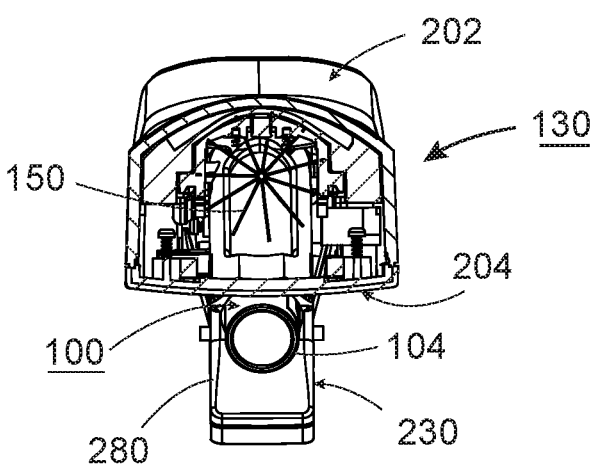

Reference is now made to FIGS. 2A-2D, which are simplified respective planar front view, two different sectional views and a pictorial cut-out view illustrations showing the medicament cartridge 100 prior to mounting into the MUCI 130, sectional views being taken along orthogonal lines C-C and D-D in FIG. 2A. Reference is additionally made to FIGS. 3A-3D, which are simplified respective planar front view, two different sectional views and a pictorial cut-out view illustrations showing the medicament cartridge 100 mounted into the MUCI 130, sectional views being taken along orthogonal lines C-C and D-D in FIG. 3A.

Figure 2D:
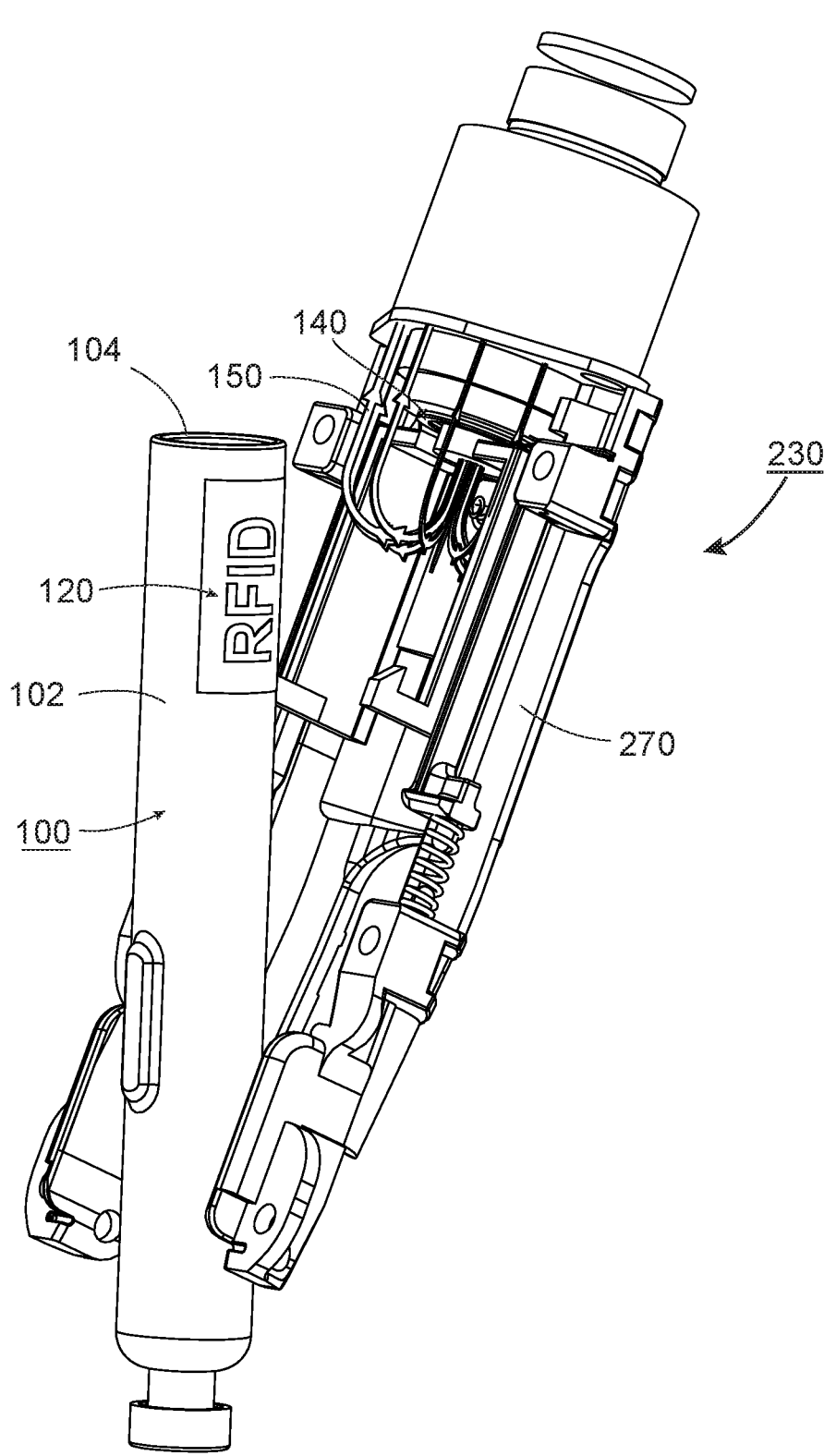
Figures 3A, 3B:
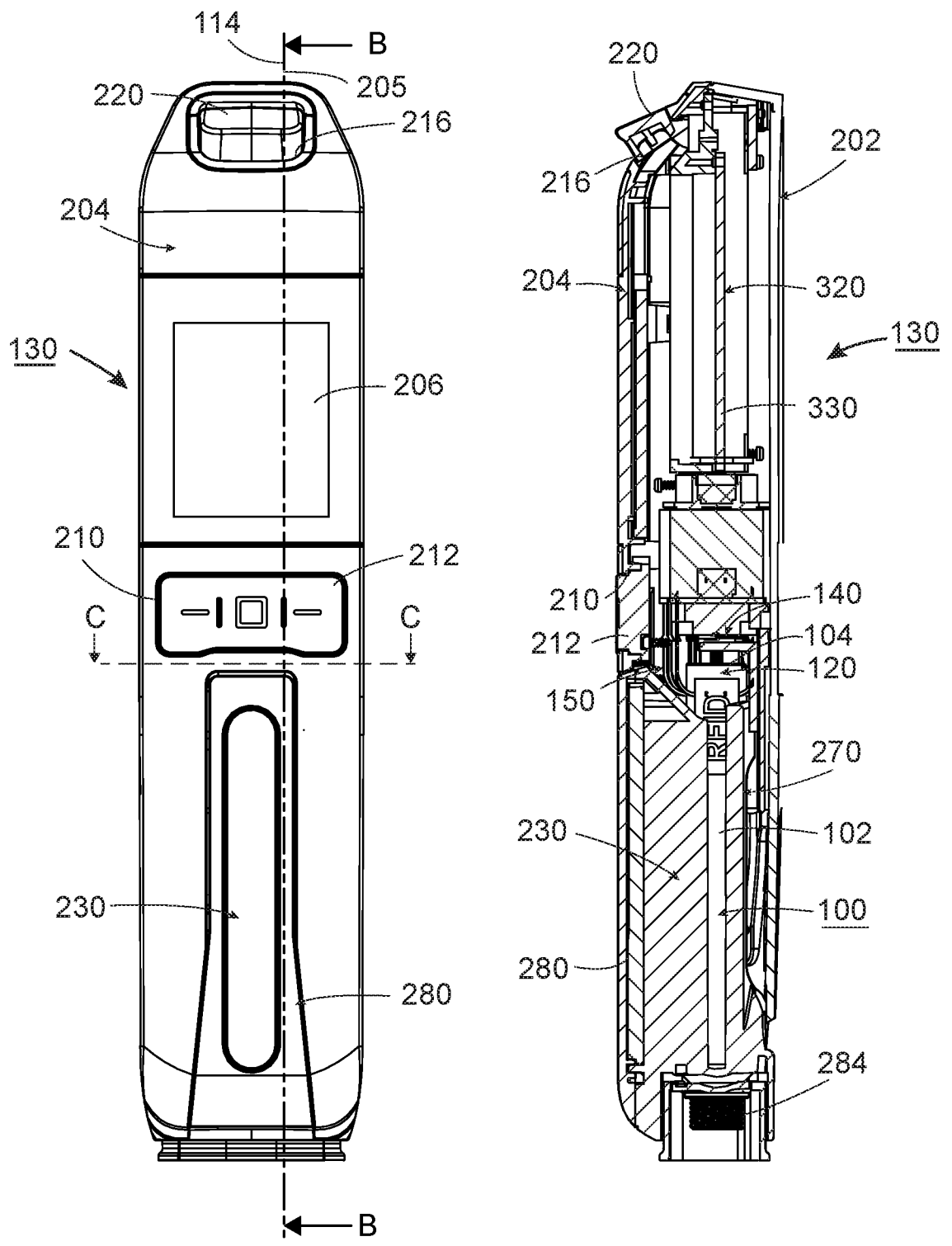
FIGS. 3A-3D are simplified respective planar front view, two different sectional views and a pictorial cut-out view illustrations showing the medicament cartridge pivotably mounted into the MUCI, sectional views being taken along orthogonal lines C-C and D-D in FIG. 3A.
Figure 3C:
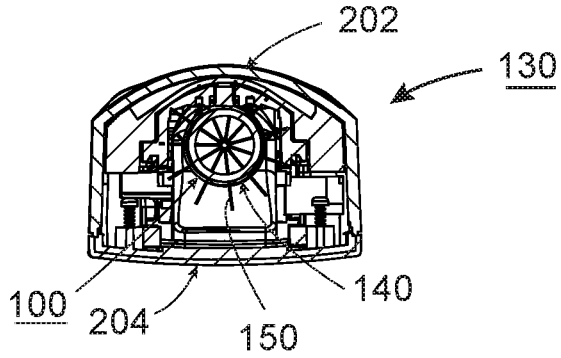
Figure 3D:
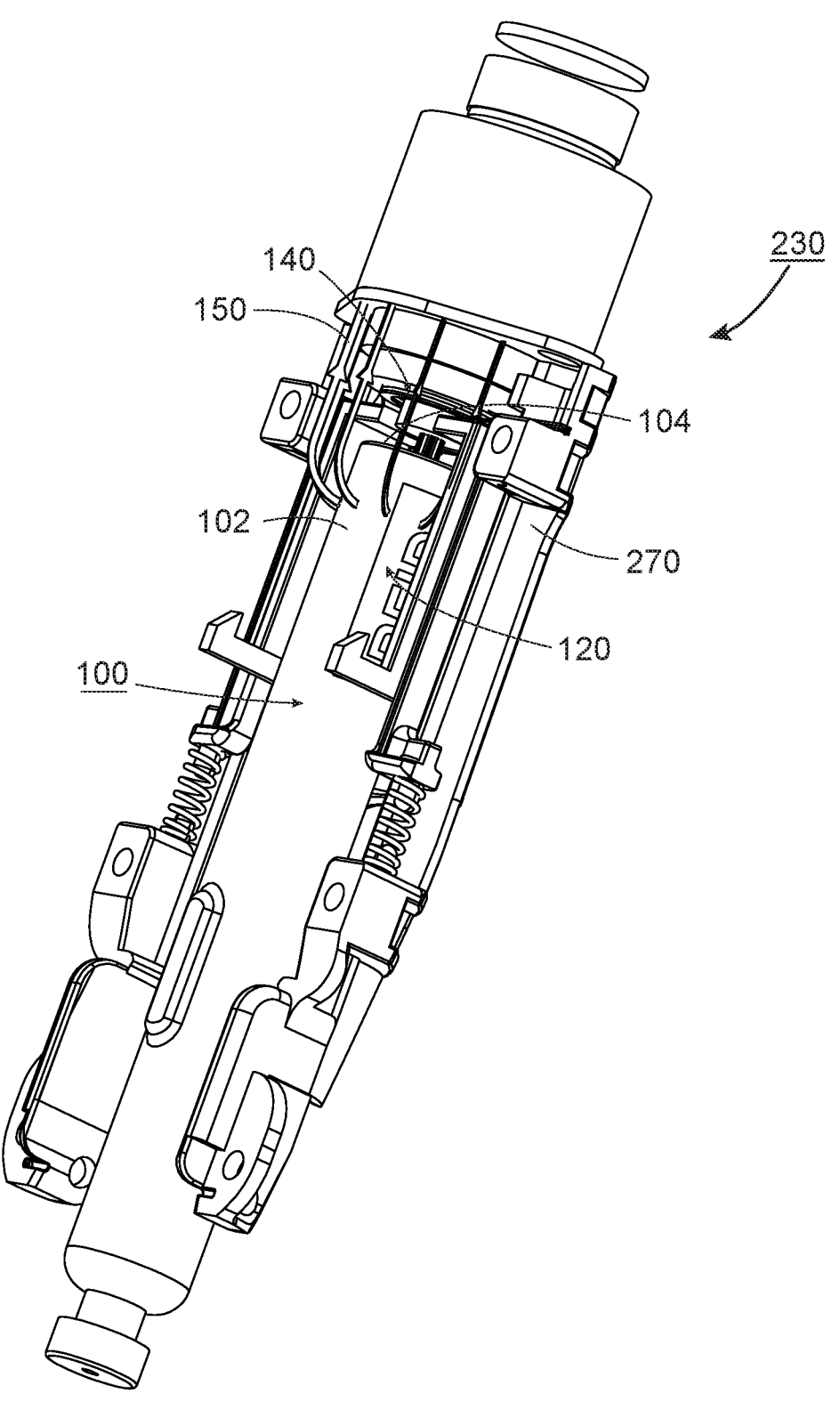

It is noted that FIGS. 2D & 3D illustrate only a portion of the cartridge enclosure assembly with the medicament cartridge 100, while omitting the remaining components of the MUCI 130 for clarity purposes.

One exemplary arrangement of the MUCI 130 in accordance with an embodiment of the present invention is such that the medicament container 100 is pivotably mounted onto the MUCI 130, as shown in FIGS. 2A-3D. FIGS. 2A-2D show an operative orientation in which the medicament cartridge 100 is not yet mounted onto the MUCI 130. FIGS. 3A-3D show an operative orientation in which the medicament cartridge 100 is mounted onto the MUCI 130. Alternatively, other MUCI 130, enabling axial or rotational mounting of the medicament cartridge 100 are also considered to be within the scope of the present invention.

Now specifically referring to the pivotably mounted medicament cartridge 100, it is seen in FIGS. 2A-3D that the MUCI 130 includes a main housing portion 202, fixedly coupled to a top housing portion 204, both arranged along a mutual longitudinal axis 205. A display 206 is preferably disposed within the MUCI 130. The top housing portion 204 preferably has an opening 210 disposed adjacent to display 206 and configured to receive a button defining element 212 (shown and described in detail in FIGS. 4A-4E of PCT Patent Application PCT/IL2017/050607) therewithin.

An opening 216 is formed at the rearward end of top housing element 104 and is configured to receive an injection button element 220 (shown and described in detail in FIGS. 5A-5D of PCT Patent Application PCT/IL2017/050607) thereinto.

It is also seen particularly in FIGS. 2A-3D that a cartridge enclosure assembly 230 (shown and described in detail in FIGS. 15A-15G of PCT Patent Application PCT/IL2017/050607) is provided to top housing portion 204 and is configured to be pivotably mounted with respect to top housing portion 204.

A main PCB assembly (shown and described in detail in FIGS. 17A-17D of PCT Patent Application PCT/IL2017/050607) is seated in the enclosure formed by housing portions 202 and 204, and is configured to be operatively coupled with a power control PCB assembly (shown and described in detail in FIGS. 18A-18C of PCT Patent Application PCT/IL2017/050607) and an electrical motor, powered by a battery.

It is seen in FIGS. 2A-3D that the cartridge enclosure assembly 230 is residing between the housing portions 202 and 204. The cartridge enclosure assembly 230 preferably includes a cartridge enclosure assembly chassis 270 and a pivot mount element 280, which is adapted to receive the medicament cartridge 100 therewithin and is generally pivotably mounted with respect to cartridge enclosure assembly chassis 270 and configured to be biased to an open operative orientation with respect to housing portions 202 and 204. The pivot mount element 280 includes a forward generally externally threaded end 284, adapted for engagement of a needle assembly therewith.

It is noted that a locking subassembly is provided as part of the MUCI 130 and is configured for selectively retaining the pivot mount element 280 of the cartridge enclosure assembly 230 in a closed operative orientation.

A piston drive subassembly 320 is also provided as part of the MUCI 130 (shown and described in detail in FIGS. 19A-19C of PCT Patent Application PCT/IL2017/050607).

When the medicament cartridge 100 having a piston is inserted into the MUCI 130, the MUCI 130 is configured to identify the medicament cartridge 100 due to the electrical communication established between the electromagnetic detector 140 and the antenna 126 of the data tag 120 and thereafter the piston drive assembly 320 is configured for axially displacing the piston within the medicament cartridge 100 in order to eject at least a portion of medicament 110 therefrom.

The piston drive subassembly 320 preferably includes electrical motor 328, which is mounted onto a plunger rod element 330 through a threaded nut. The electrical motor 328 is adapted to be operatively coupled to power control PCB assembly 254, and following receipt of a suitable signal from the CPU of MUCI 130, the electrical motor 328 causes axial displacement of the plunger rod element 330 with respect to housing portions 202 and 204.

It is noted that the MUCI 130 in accordance with an embodiment of the present invention shown in FIGS. 2A-3D works preferably as described in a previously filed PCT Patent Application PCT/IL2017/050607, filed Jun. 1, 2017, which has published as WO2017212473 and entitled "Multiple use computerized injector".

It is a particular feature of an embodiment of the present invention that the electromagnetic detector 140 is arranged within the enclosure formed by housing portions 202 and 204. It is seen that the electromagnetic detector 140 is disposed on a plane, which extends substantially perpendicularly to longitudinal axis 205.

Preferably, the electromagnetic detector 140 is fixedly mounted onto cartridge enclosure assembly chassis 270 of the cartridge enclosure assembly 230. Alternatively, the electromagnetic detector 140 may be fixedly mounted at another location within the enclosure formed between housing portions 102 and 104, such as for example surrounding the plunger rod 330 or surrounding the rearward end of the medicament cartridge 100 adjacent to the rearward edge 104 thereof. Further alternatively, the electromagnetic detector 140 may be fixedly mounted to the inner surface of the pivot mount element 280 and thus surround the medicament cartridge 100.

It is seen in FIGS. 2A-2D that the medicament cartridge 100 is inserted into the pivot mount element 280, but the pivot mount element 280 is now disposed in its open operative orientation. It is seen that in this open operative orientation, the medicament cartridge 100 may be inserted into the pivot mount element 280 at any rotational orientation and thus the orientation of the data tag 120 formed on the barrel 102 of the medicament cartridge 100 is not pre-determined.

No electrical communication is established yet between the electromagnetic detector 140 and the antenna 126 of the data tag 120 in this operative orientation and the electromagnetic detector 140 is fixedly coupled to the MUCI 130 and pending mounting of the medicament cartridge 100 thereinto for initiating electrical communication therewith.

Referring specifically to FIGS. 3A-3D, it is seen that the medicament cartridge 100 is inserted into the pivot mount element 280 and the pivot mount element 280 is now disposed in its closed operative orientation, such that longitudinal axis 114 of the medicament cartridge 100 is generally parallel to the longitudinal axis 205 of the MUCI 130 and such that the cartridge enclosure assembly 230 is locked. In this operative orientation, the rearward edge 104 of the medicament cartridge 100, thus in turn the data tag 120 is disposed in close proximity with the electromagnetic detector 140 and disposed generally in perpendicular to the plane of the electromagnetic detector 140.

It is noted that in accordance with an embodiment of the present invention, the data tag 120 is slightly spaced forwardly from the electromagnetic detector 140. Alternatively, the data tag 120 may be spaced rearwardly from the electromagnetic detector 140.

It is noted that upon mounting of the medicament cartridge 100 into the MUCI 130, resulting in closed operative orientation of the pivot mount element 280, the electromagnetic detector 140 is preferably activated by the controller of the MUCI 130 and operative to excite the data tag 120 by transmitting an electromagnetic signal to the data tag 120 and to receive a response signal therefrom. This process enables reading or writing data to the data tag 120 attached to the medicament cartridge 100.

In accordance with an embodiment of the present invention, the electromagnetic detector 140 transmits data using electromagnetic field at a certain frequency, the data tag 120 is consequently powered and the received data is processed and transmitted back to the electromagnetic detector 140.

It is known that when a data tag and an antenna are disposed on two substantially parallel planes, the strongest signal is transferred between them and if an angle exists between the planes of the data tag and the antenna, the strength of the signal transferred therebetween decreases. This fact usually results in the importance of the rotational orientation of the data tag relative to the antenna.

It is a particular feature of an embodiment of the present invention that the data tag 120 is disposed generally in perpendicular with respect to the plane of the electromagnetic detector 140, which is preferably annularly shaped, thus enabling the electromagnetic field lines 150 of the electromagnetic detector 140 to reach the data tag 120 irrespectively of the rotational orientation of the data tag

120. This effect is enabled due to the doughnut-like shape of the electromagnetic field lines 150 formed by the electromagnetic detector 140, which is formed as an annular antenna. The annular antenna provides for effective antenna area which extends around the entire circumference of the medicament cartridge 100, thus optimal signal strength between the antenna 126 of the data tag 120 and the electromagnetic detector 140 is achieved irrespectively of the rotational orientation in which the medicament cartridge 100 is mounted into the MUCI 130.

Preferably, the data tag 120 is arranged on the medicament cartridge 100 such that the long side walls 122 of the data tag 120 extend in parallel to the rearward edge 104 of the barrel 102, thus increasing the effective surface of antenna 126 that is exposed to the magnetic flux of the electromagnetic detector 140.

Electrical communication is established between the antenna 126 of the data tag 120 and the electromagnetic detector 140 upon mounting of the medicament cartridge 100 into the MUCI 130, which enables reading and/or writing data to the data tag 120. The CPU of the MUCI 130 controls the operation of the piston drive subassembly 320 based on the data received from the data tag 120.

Figures 4A, 4B:
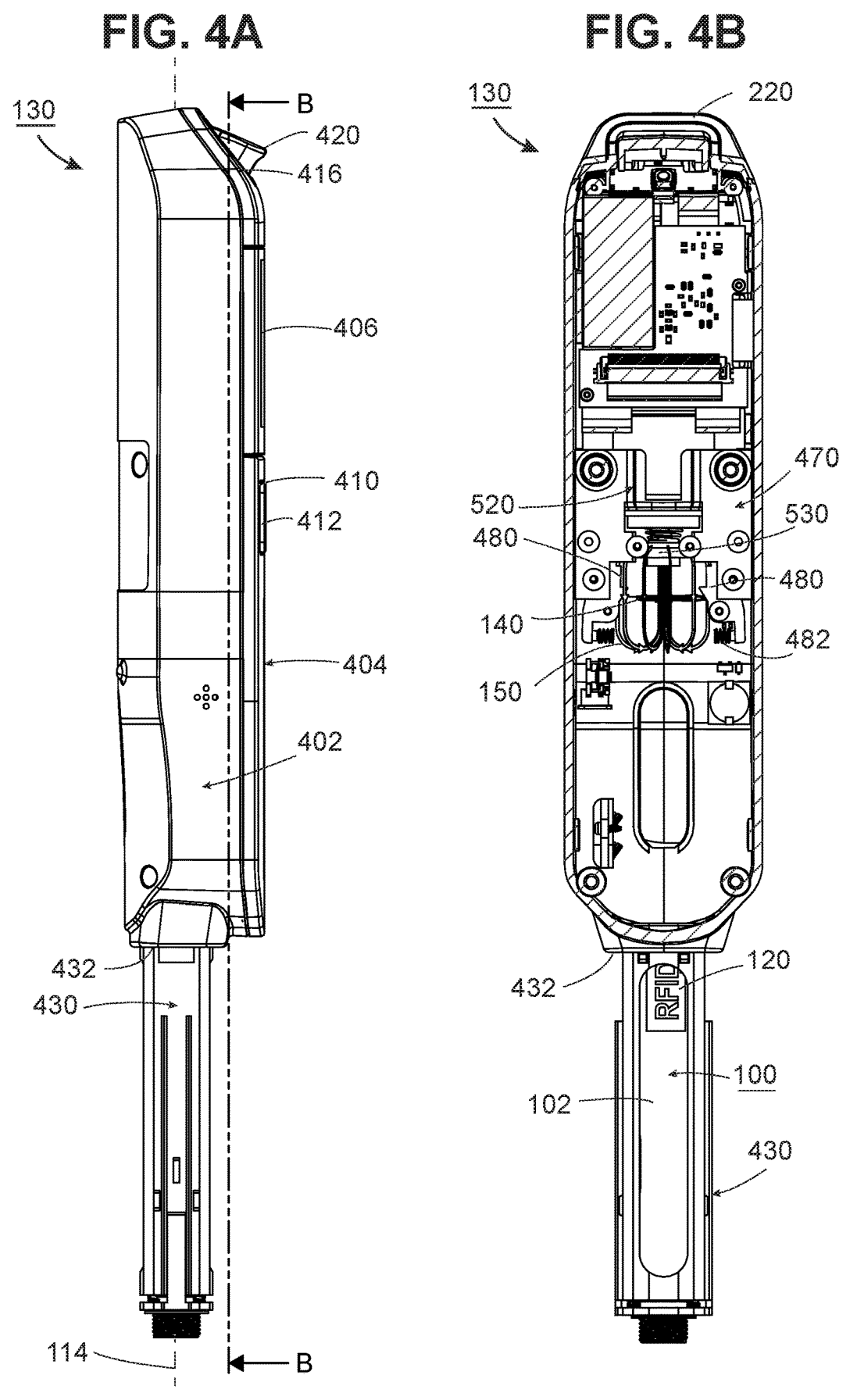
Figures 5A, 5B:
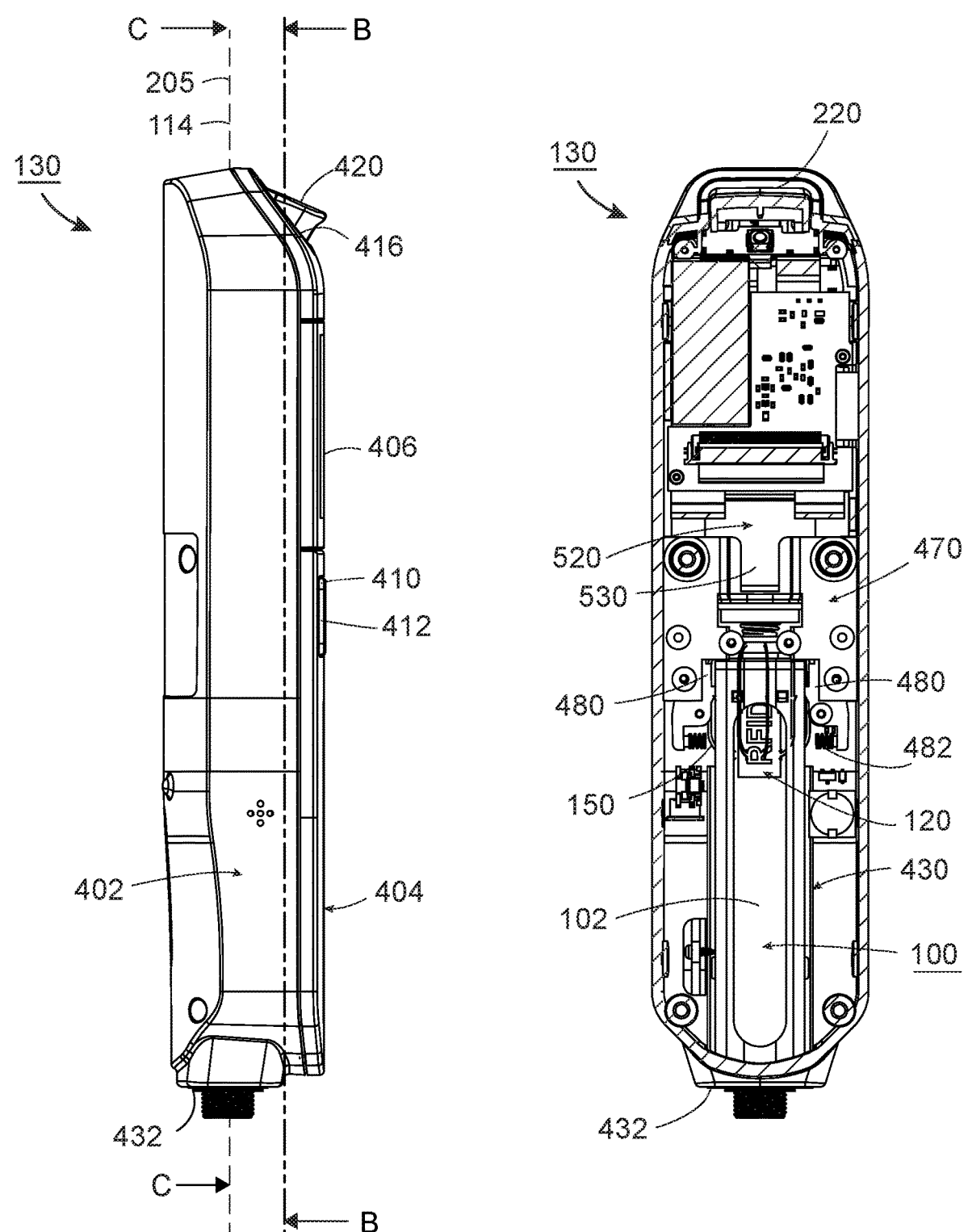
FIGS. 5A-5C are simplified respective planar side view and two different sectional view illustrations showing the medicament cartridge axially mounted into the MUCI, sectional views being taken along orthogonal lines B-B and C-C in FIG. 5A.
Figure 5C:
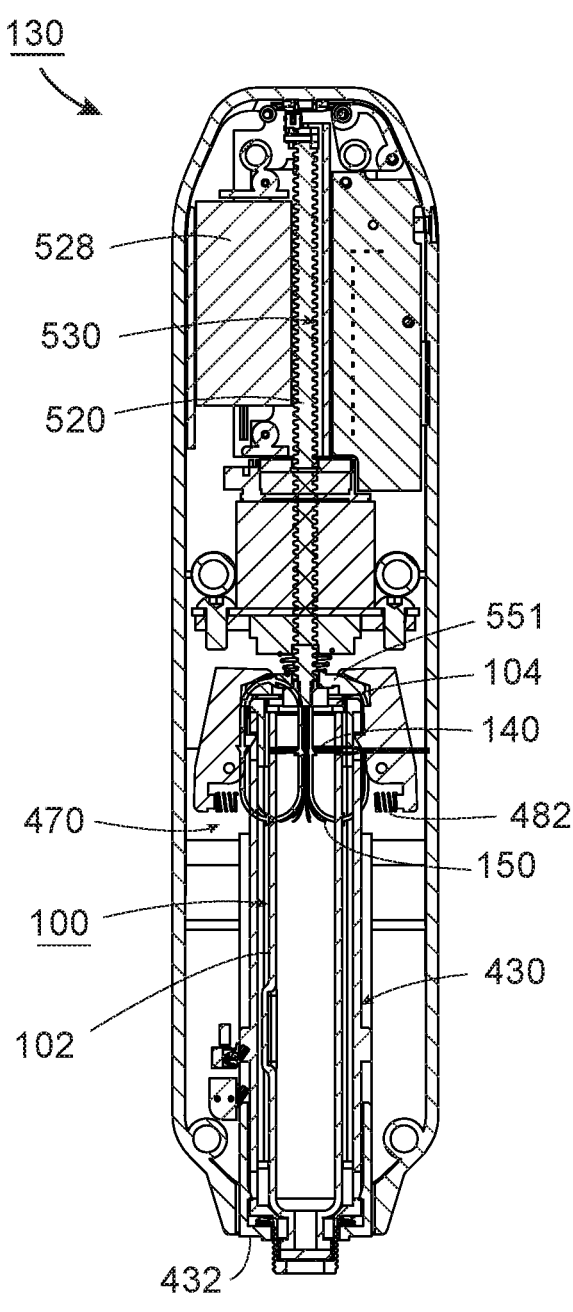

Reference is now made to FIGS. 4A-4B, which are simplified respective planar side view and a sectional view illustration showing the medicament cartridge 100 prior to axial mounting into the MUCI 130, sectional view being taken along lines B-B in FIG. 4A. Reference is additionally made to FIGS. 5A-5C, which are simplified respective planar side view and two different sectional view illustrations showing the medicament cartridge 100 axially mounted into the MUCI 130, sectional views being taken along orthogonal lines B-B and C-C in FIG. 5A.

Another exemplary arrangement of the MUCI 130 in accordance with another embodiment of the present invention is such that the medicament container 100 is axially mounted onto the MUCI 130, as shown in FIGS. 4A-4B. FIGS. 4A-4B show an operative orientation in which the medicament cartridge 100 is not yet mounted onto the MUCI 130. FIGS. 5A-5C show an operative orientation in which the medicament cartridge 100 is mounted onto the MUCI 130. Alternatively, other MUCI 130, enabling pivotable or rotational mounting of the medicament cartridge 100 are also considered to be within the scope of the present invention.

Now specifically referring to the axially mounted medicament cartridge 100, it is seen in FIGS. 4A-5C that the MUCI 130 includes a main housing portion 402, fixedly coupled to a top housing portion 404, both arranged along a mutual longitudinal axis 405. A display 406 is preferably disposed within the MUCI 130. The top housing portion 404 preferably has an opening 410 disposed adjacent to display 406 and configured to receive a button defining element 412 (shown and described in detail in FIGS. 4A-4E of PCT Patent Application PCT/IL2017/050607) therewithin.

An opening 416 is formed at the rearward end of top housing element 404 and is configured to receive an injection button element 420 (shown and described in detail in FIGS. 5A-5D of PCT Patent Application PCT/IL2017/050607) thereinto.

It is also seen particularly in FIGS. 4A-5C that the MUCI 130 is configured to axially receive a cassette assembly 430 containing a cartridge with a medicament therein through opening 432 of the main housing portion 402 into the enclosure formed between the main housing portion 402 and the top housing portion 404. The cassette 430 is configured to be selectably slidably axially displaceable along longitudinal axis 405 relative to the main and top housing portions 402 and 404.

A main PCB assembly (shown and described in detail in FIGS. 17A-17D of PCT Patent Application PCT/IL2017/050607) is seated in the enclosure formed by housing portions 402 and 404, and is configured to be operatively coupled with a power control PCB assembly (shown and described in detail in FIGS. 18A-18C of PCT Patent Application PCT/IL2017/050607) and an electrical motor, powered by a battery.

It is seen in FIG. 4B that a cassette guiding and locking element 470 is adapted to be enclosed between the main housing portion 402 and the top housing portion 404.

It is a particular feature of an embodiment of the present invention that upon axial insertion of the cassette assembly 430 into the enclosure formed by the main and top housing portions 402 and 404, the guiding and locking element 470 is configured to selectably lock the cassette assembly 430 in place by means of locking elements 480.

In accordance with an embodiment of the present invention, there are typically two generally identical locking elements 480, each of which is configured to be pivotable with respect to the cassette guiding and locking element 470 and configured to be biased to their locked orientation under the biasing force of springs 482.

A piston drive subassembly 520 is provided as part of the MUCI 130. It is noted that the piston and drive subassembly 520 functions in a similar manner to the piston drive subassembly 220 shown and described in detail in FIGS. 19A-19C of PCT Patent Application PCT/IL2017/050607. When the cassette assembly 430 having a medicament cartridge 100 is inserted into the MUCI 130, the MUCI 130 is configured to identify the medicament cartridge 100 due to the electrical communication established between the electromagnetic detector 140 and the antenna 126 of the data tag 120 that is disposed on the outer surface of the barrel 102 of the medicament cartridge 100, and thereafter the piston drive assembly 520 is configured for axially displacing the piston within the medicament cartridge 100 in order to eject at least a portion of medicament 110 therefrom.

The piston drive subassembly 520 preferably includes electrical motor 528, which is mounted onto a plunger rod element 530 through a threaded nut. The electrical motor 528 is adapted to be operatively coupled to power control PCB assembly 454, and following receipt of a suitable signal from the CPU of MUCI 130, the electrical motor 528 causes axial displacement of the plunger rod element 530 with respect to housing portions 42 and 404.

A lock release element 551 is adapted to be mounted onto the forward end of the plunger rod element 530. The lock release element 551 is configured to operatively couple the plunger rod element 530 to the locking elements 480, such that rearward displacement of the plunger rod element 530 causes pivoting of the two locking elements 480 outwardly in order to release the cassette assembly 430 from the cassette guiding and locking element 470. This operative coupling occurs due to the fact that the locking elements 480 are engaged with lock release element 551, while the lock release element is coupled to the plunger rod element 530 and is displaceable longitudinally together therewith.

It is noted that the piston drive subassembly 520 of the MUCI 130 in accordance with an embodiment of the present invention works preferably as described in a previously filed PCT Patent Application PCT/IL2017/050607, filed Jun. 1, 2017, which has published as WO2017212473 and entitled "Multiple use computerized injector".

It is a particular feature of an embodiment of the present invention that the electromagnetic detector 140 is arranged within the enclosure formed by housing portions 402 and 404. It is seen that the electromagnetic detector 140 is disposed on a plane, which extends substantially perpendicularly to longitudinal axis 405.

Preferably, the electromagnetic detector 140 is fixedly mounted to one of the housing portions 402 and 404. Alternatively, the electromagnetic detector 140 may be fixedly mounted at another location within the enclosure formed between housing portions 402 and 404, such as for example surrounding the plunger rod 530 or surrounding the rearward end of the medicament cartridge 100 adjacent to the rearward edge 104 thereof.

It is seen in FIGS. 4A and 4B that the medicament cartridge 100 is inserted into the cassette assembly 430, but the cassette assembly 430 is not yet inserted into the enclosure formed by housing portions 402 and 404. The longitudinal axis 114 of the medicament cartridge 100 is aligned with the longitudinal axis 205 of the MUCI 130 in accordance with an embodiment of the present invention.

It is a particular feature of an embodiment of the present invention that the medicament cartridge 100 may be inserted into the cassette assembly 430 at any rotational orientation and thus the orientation of the data tag 120 formed on the barrel 102 of the medicament cartridge 100 is not predetermined.

No electrical communication is established yet between the electromagnetic detector 140 and the antenna 126 of the data tag 120 in this operative orientation and the electromagnetic detector 140 is fixedly coupled to the MUCI 130 and pending mounting of the medicament cartridge 100 thereinto for initiating electrical communication therewith.

Referring specifically to FIGS. 5A-5C, it is seen that the medicament cartridge 100 is inserted into the cassette assembly 430 and the cassette assembly 430 is now inserted into the enclosure between housing portions 402 and 404 and is locked therein. In this operative orientation, the rearward edge 104 of the medicament cartridge 100, thus in turn the data tag 120 is disposed in close proximity with the electromagnetic detector 140 and disposed generally in perpendicular to the plane of the electromagnetic detector 140.

It is noted that in accordance with an embodiment of the present invention, the data tag 120 is slightly spaced forwardly from the electromagnetic detector 140. Alternatively, the data tag 120 may be spaced rearwardly from the electromagnetic detector 140.

It is noted that upon mounting of the cassette assembly 430 with the medicament cartridge 100 into the MUCI 130, resulting in locked operative orientation of the cassette assembly 430, the electromagnetic detector 140 is preferably activated by the controller of the MUCI 130 and operative to excite the data tag 120 by transmitting an electromagnetic signal to the antenna 126 of the data tag 120 and to receive a response signal therefrom. This process enables reading or writing data to the data tag 120 attached to the medicament cartridge 100.

In accordance with an embodiment of the present invention, the electromagnetic detector 140 transmits data using electromagnetic field at a certain frequency, the data tag 120 is consequently powered and the received data is processed and transmitted back to the electromagnetic detector 140.

It is known that when a data tag and an antenna are disposed on two substantially parallel planes, the strongest signal is transferred between them and if an angle exists between the planes of the data tag and the antenna, the strength of the signal transferred therebetween decreases. This fact usually results in the importance of the rotational orientation of the data tag relative to the antenna.

It is a particular feature of an embodiment of the present invention that the data tag 120 is disposed generally in perpendicular with respect to the plane of the electromagnetic detector 140, which is preferably annularly shaped, thus enabling the electromagnetic field lines of the electromagnetic detector 140 to reach the data tag 120 irrespectively of the rotational orientation of the data tag 120. This effect is enabled due to the doughnut-like shape of the electromagnetic field lines formed by the electromagnetic detector 140, which is formed as an annular antenna. The annular antenna provides for effective antenna area which extends around the entire circumference of the medicament cartridge 100, thus optimal signal strength between the antenna 126 of the data tag 120 and the electromagnetic detector 140 is achieved irrespectively of the rotational orientation in which the medicament cartridge 100 is mounted into the MUCI 130.

Preferably, the data tag 120 is arranged on the medicament cartridge 100 such that the long side walls 122 of the data tag 120 extend in parallel to the rearward edge 104 of the barrel 102, thus increasing the effective surface of antenna 126 that is exposed to the magnetic flux of the electromagnetic detector 140.

Electrical communication is established between the antenna 126 of the data tag 120 and the electromagnetic detector 140 upon mounting of the cassette assembly 430 with the medicament cartridge 100 into the MUCI 130, which enables reading and/or writing data to the data tag 120. The CPU of the MUCI 130 controls the operation of the piston drive subassembly 520 based on the data received from the data tag 120.

It is noted that alternative medicament cartridge 100 insertion methods into the MUCI 130 are considered to be within the scope of the present invention, such as for example providing an opening at the forward end of the housing of MUCI 130 and rotatably inserting the medicament cartridge 100 therethrough. Other methods of medicament cartridge 100 insertion into the MUCI 130 are also considered to be within the scope of the present invention.

It will be appreciated by persons skilled in the art that the present invention is not limited by what has been particularly shown and described hereinabove. Rather the present invention includes both combinations and subcombinations of various features described herein and improvements and variations which would occur to persons skilled in the art upon reading the foregoing description and which are not in the prior art.

The invention claimed is:

1. A computer-controlled injector, comprising:
a housing arranged along a longitudinal axis and configured to receive a medicament cartridge;
an injection drive mechanism comprising a computer-controlled motor for driving a piston, forming part of said medicament cartridge, for injecting a medicament;
a data tag attachable to said medicament cartridge; and
an electromagnetic detector disposed within said housing and being connectable to the data tag upon mounting of said medicament cartridge into said housing, said electromagnetic detector permitting data to be read from or written to said data tag, the electromagnetic detector comprising at least one annular antennas extending around a circumference of the medicament cartridge, wherein said electromagnetic detector is configured to read or write data to said data tag irrespectively of a rotational orientation of said medicament cartridge within said computer-controlled injector.

2. The computer-controlled injector of claim 1, wherein said electromagnetic detector comprises a single antenna.

3. The computer-controlled injector of claim 1, wherein said electromagnetic detector is configured to generate electromagnetic field lines that extend around entire circumference of said medicament cartridge.

4. The computer-controlled injector of claim 1, wherein said housing comprises an opening at a forward end thereof and said medicament cartridge is adapted for axial insertion into said housing through said opening.

5. The computer-controlled injector of claim 1, wherein a pivoting openable and closeable mounting portion is provided to said housing and adapted to receive said medicament cartridge.

6. The computer-controlled injector of claim 1, wherein said housing comprises an opening at a forward end thereof and said medicament cartridge is adapted for rotatable insertion into said housing through said opening.

7. The computer-controlled injector of claim 1, wherein said data tag comprises a passive device.

8. The computer-controlled injector of claim 1, wherein said data tag comprises an active device.

9. A medicament delivery system, comprising:
a computer-controlled injector arranged along a longitudinal axis and having a housing and an electromagnetic detector contained therewithin, the electromagnetic detector comprising at least one annular antenna extending around a circumference of a medicament cartridge;
said medicament cartridge having a data tag formed thereon; and
said electromagnetic detector being operative to communicate with said data tag upon mounting of said medicament cartridge into said computer-controlled injector such that said data tag is disposed in proximity with said electromagnetic detector,
wherein said electromagnetic detector configured to read or write data to said data tag irrespectively of a rotational orientation of said medicament cartridge within said computer-controlled injector.

10. The medicament delivery system of claim 9, wherein said electromagnetic detector comprises a single antenna.

11. The medicament delivery system of claim 9, wherein said data tag comprises a passive device.

12. The medicament delivery system of claim 9, wherein said data tag comprises an active device.

13. The medicament delivery system of claim 9, wherein said housing comprises an opening at a forward end thereof and said medicament cartridge is adapted for axial insertion into said housing through said opening.

14. The medicament delivery system of claim 9, wherein said housing comprises an opening at a forward end thereof and said medicament cartridge is adapted for rotatable insertion into said housing through said opening.

15. A computer-controlled injector for use with a medicament cartridge, which has a medicament contained therewithin and a data tag attached thereto, said computer-controlled injector comprising:
an injection drive mechanism comprising a computer-controlled motor for driving a piston, forming part of said medicament cartridge, for injecting a medicament;
a medicament cartridge mounting portion configured to support an electromagnetic detector; and
said electromagnetic detector configured to read or write data to said data tag when said medicament cartridge is mounted onto said medicament cartridge mounting portion and comprising at least one annular antennas extending around a circumference of the medicament cartridge, and wherein said electromagnetic detector configured to read or write data to said data tag irrespectively of a rotational orientation of said medicament cartridge within said computer-controlled injector.

16. The computer-controlled injector of claim 15, wherein said electromagnetic detector comprises a single antenna.

17. The computer-controlled injector of claim 15, wherein said electromagnetic detector is configured to generate electromagnetic field lines that extend around entire circumference of said medicament cartridge.

\* \* \* \* \*